US009475771B2

(12) United States Patent
Renga et al.

(10) Patent No.: US 9,475,771 B2
(45) Date of Patent: *Oct. 25, 2016

(54) PROCESS FOR THE PREPARATION OF 4-ALKOXY-3-HYDROXYPICOLINIC ACIDS

(71) Applicant: DOW AGROSCIENCES LLC, Indianapolis, IN (US)

(72) Inventors: James M. Renga, Spokane, WA (US); Yuanming Zhu, Carmel, IN (US); Gregory T. Whiteker, Carmel, IN (US); Nakyen Choy, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/794,471

(22) Filed: Jul. 8, 2015

(65) Prior Publication Data

US 2016/0009676 A1    Jan. 14, 2016

Related U.S. Application Data

(60) Provisional application No. 62/021,876, filed on Jul. 8, 2014, provisional application No. 62/021,877, filed on Jul. 8, 2014, provisional application No. 62/021,881, filed on Jul. 8, 2014.

(51) Int. Cl.
*C07D 213/79* (2006.01)
*C07D 213/803* (2006.01)
*C07D 307/54* (2006.01)
*C07D 213/84* (2006.01)

(52) U.S. Cl.
CPC ........... *C07D 213/84* (2013.01); *C07D 213/79* (2013.01); *C07D 213/803* (2013.01); *C07D 307/54* (2013.01)

(58) Field of Classification Search
None
See application file for complete search history.

(56) References Cited

U.S. PATENT DOCUMENTS

| | | | |
|---|---|---|---|
| 4,406,905 A | 9/1983 | Zahner et al. | |
| 4,506,084 A | 3/1985 | Kay et al. | |
| 6,355,660 B1 | 3/2002 | Ricks | |
| 6,521,622 B1 | 2/2003 | Ricks | |
| 6,706,740 B2 | 3/2004 | Ricks | |
| 6,861,390 B2 | 3/2005 | Meyer | |
| 6,927,225 B2 | 8/2005 | Ricks | |
| 7,034,035 B2 | 4/2006 | Ricks | |
| 7,183,278 B1 | 2/2007 | Imamura | |
| 7,250,389 B1 | 7/2007 | Sakanaka | |
| 8,785,479 B2 | 7/2014 | Meyer | |
| 8,835,462 B2 | 9/2014 | Meyer | |
| 8,883,811 B2 | 11/2014 | Owen | |
| 2002/0177578 A1 | 11/2002 | Ricks | |
| 2003/0018012 A1 | 1/2003 | Ricks | |
| 2003/0018052 A1 | 1/2003 | Ricks | |
| 2003/0022902 A1 | 1/2003 | Ricks | |
| 2004/0034025 A1 | 2/2004 | Ricks | |
| 2004/0048864 A1 | 3/2004 | Ricks | |
| 2004/0171838 A1 | 9/2004 | Meyer | |
| 2004/0186296 A1 | 9/2004 | Nyaz | |
| 2004/0192924 A1 | 9/2004 | Meyer et al. | |
| 2005/0176767 A1 | 8/2005 | Chan Chun Kong et al. | |
| 2005/0239873 A1 | 10/2005 | Hockenbery | |
| 2007/0060579 A1 | 3/2007 | Wachendorff-Neumann | |
| 2007/0066629 A1 | 3/2007 | Tormo | |
| 2009/0306142 A1 | 12/2009 | Carson | |
| 2011/0053966 A1 | 3/2011 | Klittich et al. | |
| 2011/0082162 A1 | 4/2011 | Lorsbach et al. | |
| 2012/0245031 A1 | 9/2012 | Gewehr et al. | |
| 2013/0296371 A1 | 11/2013 | Meyer | |
| 2013/0296373 A1 | 11/2013 | Meyer et al. | |
| 2014/0128411 A1 | 5/2014 | Ogawa et al. | |
| 2014/0187587 A1 | 7/2014 | Ouimette | |
| 2014/0187588 A1 | 7/2014 | Lalonde | |
| 2014/0275171 A1 | 9/2014 | Meyer | |
| 2015/0065529 A1 | 3/2015 | Owen | |

FOREIGN PATENT DOCUMENTS

| | | |
|---|---|---|
| EP | 1516874 | 3/2005 |
| WO | 01/14339 | 3/2001 |
| WO | 2009/040397 | 9/2008 |
| WO | 2012/070015 | 5/2012 |

OTHER PUBLICATIONS

Y.Usuki, et al. Journal of Antibiotics, vol. 55, No. 6, Jun. 2002, pp. 607-610.
Gisi, U. The American Phytopathological Society, vol. 86, No. 11, 1996, pp. 1273-1279.
Anonymous, Synergistic Fungicidal Composition of Heterocyclic Aromatic Amides and Triazoles, IP.COM, Electronic Publication, 2004, 11 pages.
Anonymous, Synergistic Fungicidal Composition of Heterocyclic Aromatic Amides and Triazoles, IP.COM Journal, IP.COM, Inc., West Henrietta, NY, US, dated Jul. 2004, 10 pages.
K. Tani, et al., Journal of Antibiotics, vol. 55, No. 3, Mar. 2002, pp. 315-321.
Z. Hu, et al, Synthesis of Novel Analogues of Antimycin A3, Tetrahedron Letters 49 (2008) pp. 5192-5195.
Kissling, Crop Protection pipeline value jumps to €2.4 billion. BASF. Mar. 11, 2010, pp. 1-4, [retrieved on Feb. 4, 2014]. Retrieved from the Internet: <URL: http://www.agro.basf.com/agr/AP-Internet/en/content/news_room/news/basf-crop-protection-pipeline-value>.
BASF new fungicide Xemium got full approval in EU. AgroNews. Jul. 18, 2012 [retrieved on 1-20 Feb. 4, 2014). Retrieved from the Internet: <URL: http://news.agropages.com/News/NewsDetail—7386.htm>.

(Continued)

*Primary Examiner* — Zinna Northington Davis
(74) *Attorney, Agent, or Firm* — Charles W. Arnett; Faegre Baker Daniels LLP

(57) ABSTRACT

4,6-Dibromo-3-hydroxypicolinonitrile may be prepared from furfural in a series of chemical steps selected from cyano-amination, amine salt formation and bromination-rearrangement. 4-Alkoxy-3-hydroxypicolinic acids may be conveniently prepared from 4,6-dibromo-3-hydroxypicolinonitrile in a series of chemical steps selected from bromo substitution, nitrile hydrolysis and halogen reduction.

9 Claims, No Drawings

(56) References Cited

OTHER PUBLICATIONS

International Searching Authority, International Search Report for PCT/US15/39565, dated Sep. 29, 2015, 3 pages.
International Searching Authority, Written Opinion for PCT/US15/39565, dated Sep. 29, 2015, 3 pages.
International Searching Authority, International Search Report for PCT/US15/39568, dated Oct. 13, 2015, 3 pages.
International Searching Authority, Written Opinion for PCT/US15/39568, dated Oct. 13, 2015, 4 pages.
International Searching Authority, International Search Report for PCT/US15/36569, dated Oct. 1, 2015, 2 pages.
International Searching Authority, Written Opinion for PCT/US15/39569, dated Oct. 1, 2015, 3 pages.
PUBCHEM-CID-11435037 Create Date: Oct. 26, 2006, 10 pages.
Goldberg, AA, et al., "254. Synthesis of Omega-Aminoalkyl Cyanides" Journal of the Chemical Society, 1947, pp. 1369-1371.
Clauson-Kass, N, et al, "Preparation of Derivatives of 3-Hydroxypicolinic Acid from Furfural", Acta Chemica Scandinavica, 1965, vol. 199, pp. 1147-1152.
Baruah, P.K, et al., "Synthesis, anticonvulsant activity, and neuropathic pain attenuating activity of N-benzyl 2-amino-2-(hetero)aromatic acetamides," Bioorganic & Medicinal Chemistry 20, (2012) 3551-3564.
Demir, A.S., et al, "An asymmetric sythesis of both enantiomers of 2,2,2-trifluror-1-furan-2-yl-ethylamine and 3,3,3-trifluoroalanine from 2,2,2-trifluroro-1-furan-2-yl-ethanone," Tetrahedron: Asymmetry 12 (2001) 2309-2313.
Guo-Qiang Shi, "delta, epsilon-Unsaturated beta,beta-Difluroro-alpha-keto Esters: Novel Synthesis and Utility as Precursors of beta,beta-Difluoro-alpha-amino Acids," Journal Organic Chemistry, 1995, 60 pp. 6289-6295.

PROCESS FOR THE PREPARATION OF 4-ALKOXY-3-HYDROXYPICOLINIC ACIDS

This application claims the benefit of U.S. Provisional Patent Application Ser. No. 62/021,876 filed Jul. 8, 2014, Ser. No. 62/021,877 filed Jul. 8, 2014, and Ser. No. 62/021,881 filed Jul. 8, 2014 each of which is expressly incorporated by reference herein in its entirety as if each were incorporated by reference herein individually.

FIELD

The present disclosure concerns a process for the preparation of 4-alkoxy-3-hydroxypicolinic acids. More particularly, the present disclosure concerns a process for the preparation of 4-alkoxy-3-hydroxypicolinic acids from furfural.

BACKGROUND

U.S. Pat. No. 6,521,622 B1 and U.S. Application Ser. Nos. 61/747,723 and 14/142,183, the disclosures of which are hereby incorporated by reference in their entireties, describe inter alia certain heterocyclic aromatic amide compounds of general Formula and their use as fungicides.

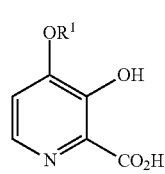

These disclosures also describe the preparation of 4-alkoxy-3-hydroxypicolinic acids as key intermediates in the preparation of these heterocyclic aromatic amide compounds. It would be useful to have an efficient and scalable process route to 4-alkoxy-3-hydroxypicolinic acids from inexpensive raw materials.

SUMMARY

The present disclosure concerns processes for the preparation of 4-alkoxy-3-hydroxypicolinic acids of Formula H

H

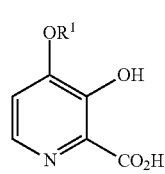

wherein $R^1$ is a $C_1$-$C_3$ alkyl;
from the compound of Formula A

A

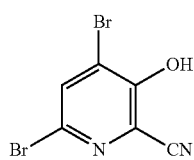

One aspect of the present disclosure are the novel intermediates produced in the present processes, viz., compounds selected from the group consisting of:

a)

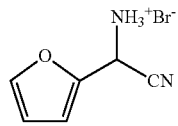

b)

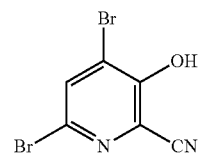

c)

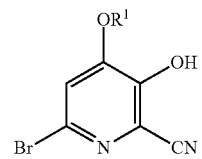

wherein $R^1$ is a $C_1$-$C_3$ alkyl;

d)

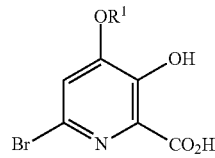

wherein $R^1$ is a $C_1$-$C_3$ alkyl; and e)

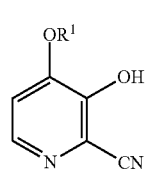

wherein $R^1$ is a $C_1$-$C_3$ alkyl.

DETAILED DESCRIPTION

The terms "isolate," "isolating," or "isolation" as used herein mean to partially or completely remove the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from ≤50% to ≥50%, and may be purified to a higher purity level using standard purification methods. The isolated product may also be used in a subsequent process step with or without purification.

In the processes described herein 4-alkoxy-3-hydroxypicolinic acids are prepared from furfural in a series of chemical steps involving cyano-amination, ammonium salt formation, bromination/rearrangement, bromo substitution by an alkoxide group, nitrile hydrolysis, and halogen reduction. Some of the individual steps may be performed in different sequences of order.

Cyano(furan-2-yl)methanaminium chloride salts of Formula 1a have been prepared and used as intermediates in the preparation of 3-hydroxpicolinonitriles and 3-hydroxy-picolinoamides of Formula 1b as described in *Acta Chem. Scand.* 19 (1965) pg. 1147-1152,

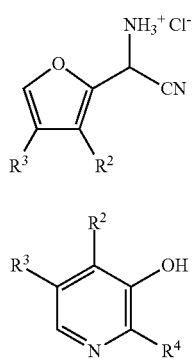

wherein $R^2$ is H or methyl, $R^3$ is H or 2-propyl, and $R^4$ is CN or $C(O)NH_2$.

A. Preparation of Compound of Formula A

In the process described herein, chemical steps a, b and c are performed as depicted in Scheme I to prepare dibromohydroxypicolinonitrile A.

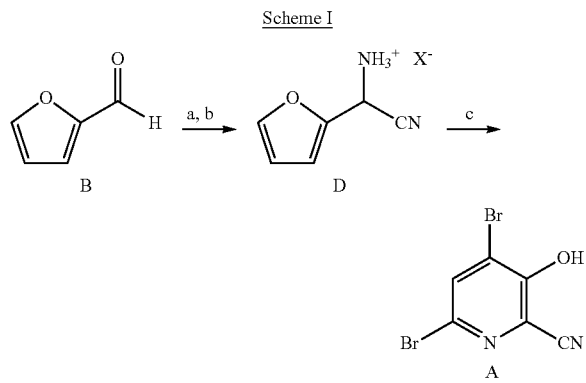

The cyano(furan-2-yl)methanaminium halide salt of Formula D is prepared by first reacting furfural (Formula B) with at least one equivalent each of an ammonia source and

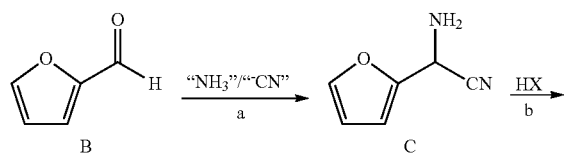

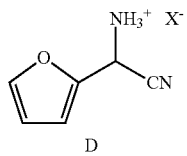

a cyanide source (Step a) in a reaction known in the art as the Strecker synthesis of α-aminonitriles which is described in *Organic Syntheses*, Coll. Vol. I, page 21 and Coll. Vol. III, pages 84 and 88 to provide the amino(furan-2-yl)acetonitrile of Formula C. Suitable ammonia sources include: ammonium salts such as, but not limited to, ammonium acetate, ammonium bromide, ammonium chloride, ammonium formate, ammonium sulfate and ammonium cyanide; ammonia dissolved in an organic solvent such as, for example, ammonia in methanol, ammonia in ethanol and ammonia in dioxane; ammonia in water (i.e., ammonium hydroxide); and liquid, anhydrous ammonia or gaseous ammonia. Suitable cyanide sources include: cyanide salts such as, but not limited to, sodium cyanide, potassium cyanide and ammonium cyanide; and hydrogen cyanide which may be added in a continuous-addition manner with ammonia to the furfural. The reaction may be carried out in a protic solvent or reaction medium such as water or an alcohol, or mixtures of water and an alcohol such as, for example, water-methanol or water-ethanol, or mixtures of water with a polar, water soluble organic solvent such as, for example, tetrahydrofuran, DMSO, dioxane and acetonitrile, or mixtures thereof. Alternatively, this reaction (Step a) may be carried out in a 2-phase solvent system consisting of water and at least one water immiscible solvent selected from, but not limited to, diethyl ether, methyl t-butyl ether (MTBE), ethyl acetate, methylene chloride, 2-methyltetrahydrofuran (2-MeTHF), toluene and xylene. Such a reaction has been described in WO Application 2000049008, page 55. The present reaction is typically conducted with agitation sufficient to maintain an essentially uniform mixture of the reactants. A typical reaction generally may require from about 1 to about 50 hours to proceed to completion. Such a reaction may be conducted at temperatures between about 0° C. and about 50° C., or preferably at temperatures between about 0° C. and about 30° C. After the reaction is complete, the amino(furan-2-yl)acetonitrile of Formula C may be recovered by employing standard isolation and purification techniques or it may be directly converted to the compound of Formula D without discreet isolation of the product of Formula C. It may be preferable to directly convert the product of Formula C into the salt of Formula D rather than storing it for extended periods.

In Step b of the sequence of reactions to prepare the compound of Formula D, at least one equivalent of a mineral acid is added to the intermediate amino(furan-2-yl)acetonitrile product of Formula C dissolved in a water immiscible solvent such as, for example, diethyl ether, MTBE, ethyl acetate, 2-MeTHF, toluene, xylene, or mixtures thereof, to provide the desired cyano(furan-2-yl)methanaminium salt of Formula D. Suitable mineral acids may include, but are not limited to, hydrobromic acid (HBr), nitric acid ($HNO_3$), sulfuric acid ($H_2SO_4$), and phosphoric acid ($H_3PO_4$). The present reaction may be conducted at temperatures of from about 0° C. to about 25° C. After the reaction is complete the desired product is recovered by employing standard isolation and purification techniques.

In the bromination/rearrangement reaction (Scheme I, Step c), the cyano(furan-2-yl)methanaminium salt of Formula D is reacted with a brominating agent to provide the brominated/rearrangement product of Formula A. The starting material of Formula D as the bromide salt, for example, may be treated with a suitable brominating agent such as bromine, 1,3-dibromo-5,5-dimethylhydantoin or N-bromosuccinimide. From about 3 to about 6 molar equivalents of the brominating agent may be used. The reaction is preferably conducted using about 3-5 molar equivalents of bromine and the bromide salt of the compound of Formula D (X=Br). It is often convenient to use an excess of the brominating agent such as a 5%, 10% or 15% molar excess, to insure the reaction proceeds to completion. The reaction is preferably carried out in a protic solvent or reaction medium such as water, or mixtures of water and a water soluble, organic solvent such as, for example, methanol,

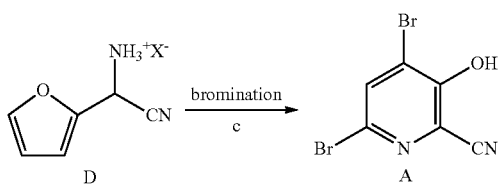

ethanol, tetrahydrofuran, dioxane or acetonitrile. The temperature at which the reaction is conducted is between about 0° C. and about 60° C. and preferably between about 0° C. and about 40° C. Upon completion of the addition of the brominating agent, the reaction mixture may be allowed to stir at room temperature for 10-48 hours. Optionally, the reaction time may be shortened by adding a base, such as, for example, 2-4 molar equivalents of sodium acetate, to the reaction. Optionally, after addition of the brominating agent is complete, the reaction may be heated at 30-60° C. to complete conversion to the product of Formula A. After the reaction is complete the desired product is recovered by employing standard isolation and purification techniques.

An embodiment of the present disclosure involves the preparation of the compound of Formula A in a "one-pot" process from furfural. In such a process all reaction steps may be conducted in a single vessel whereby the reactants and reagents are sequentially added to the vessel and then, after completion of chemical steps a and c, an isolation operation is conducted to isolate the product of Formula A. Using the chemical reactants and reagents described herein, a cyanide source, an ammonium source and furfural are combined together in a reaction vessel with a solvent and sufficiently agitated at a suitable temperature and

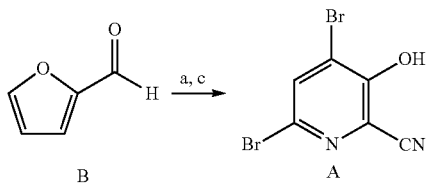

for a suitable time to produce the amino(furan-2-yl)acetonitrile product of Formula C. The resulting reaction mixture containing the product of Formula C is then treated with a brominating agent, such as bromine, optionally using a base, and utilizing suitable reaction conditions (time, temperature and/or solvent) as described herein to provide the product of Formula A. The product of Formula A is then recovered from the reaction mixture and purified as needed by employing standard isolation and purification techniques.

Another embodiment of the present disclosure involves preparation of the compound of Formula A by a process referred to herein as the biphasic process. "Biphasic process" as used herein refers to a process that employs a 2-phase solvent system. As such, a 2-phase solvent system for the Strecker synthesis of the α-aminoacetonitrile of Formula C was used employing the conditions, chemical reactants and reagents described herein. Use of the 2-phase solvent system, which includes water and a water-immiscible organic solvent, allows for easy separation of water soluble salts present after the Strecker reaction (i.e., cyanide and acetate salts). The α-aminoacetonitrile product remaining in the organic solvent is then extracted into an aqueous hydrobromic acid (HBr) solution by formation of the corresponding water soluble HBr salt (compound of Formula D; X=Br). Treatment of the resulting aqueous solution of the HBr salt of the α-aminoacetonitrile with bromine affords the product of Formula A. The product of Formula A is then recovered from the final reaction mixture and purified as needed by employing standard isolation and purification techniques. The biphasic process may be conducted at temperatures between about 0° C. and about 50° C. or preferably between about 15° C. and about 35° C.

Another embodiment of the present disclosure involves the preparation of the compound of Formula A in a process comprising two chemical steps (i.e, the two-step process) from the cyano(furan-2-yl)methanaminium salt of Formula D, wherein X is as described herein. In such a process, the compound of Formula D is first reacted with from about 1 to about 2 molar equivalents of a brominating agent to provide the 3-hydroxy-picolinonitrile product of Formula J. The product of Formula J is then recovered by employing standard isolation and purification techniques and is then treated with from about 2 to about 3 molar equivalents of the brominating agent to furnish the product of Formula A.

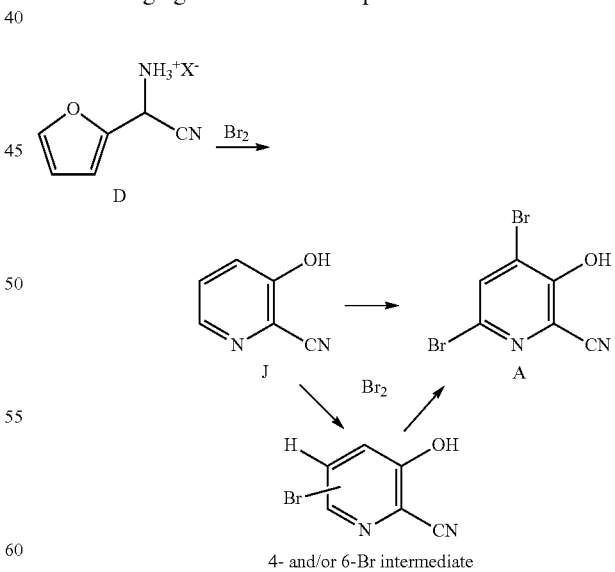

4- and/or 6-Br intermediate

The two-step process may be conducted using bromine and the bromide salt of the compound of Formula D (X=Br). It is often convenient to use an excess of the brominating agent such as a 5%, 10% or 15% molar excess, to insure the individual reactions proceed to completion. There may be small amounts of the intermediate mono-brominated products (i.e., 4-bromo- and/or 6-bromo-3-hydroxypicolinonitrile) present in the isolated product of Formula A. The reactions for the 2-step process may be carried out in a protic solvent or reaction medium such as water, or mixtures of water and a water soluble, organic solvent such as, for example, methanol, ethanol, tetrahydrofuran, dioxane or acetonitrile. The temperature at which the reactions may be conducted are between about 0° C. and about 75° C. Upon completion of the addition of the brominating agent, the reaction mixture may be allowed to stir at room temperature for 0-48 hours. Optionally, the conversion of the compound of Formula J to the compound of Formula A with a brominating agent may be conducted with an added base such as, for example, 2-4 molar equivalents of sodium acetate. After the reactions are complete the desired product is recovered by employing standard isolation and purification techniques.

B. Preparation of Compound of Formula H

The chemical steps d, e and f may be performed as depicted in Scheme II in two different sequences to prepare the 4-alkoxy-3-hydroxypicolinic acid of Formula H. In the substitution reaction to replace the 4-bromo group of the compound of Formula A with an alkoxy group (Step d), use of an alkali metal alkoxide of formula $MOR^1$ (M is an alkali metal; $R^1$ is a $C_1$-$C_3$ alkyl) produces the 4-alkoxy-6-bromo-3-hydroxypicolinonitrile of Formula F. At least 2 equivalents, and preferably 2-5 equivalents, of the alkali metal alkoxide are used in this reaction. Typical alkali metal alkoxides useful in this reaction include sodium or potassium, methoxide, ethoxide, 1-propoxide or 2-propoxide. The reaction may be carried out in a protic solvent or reaction medium such as methanol (for methoxide), ethanol (for

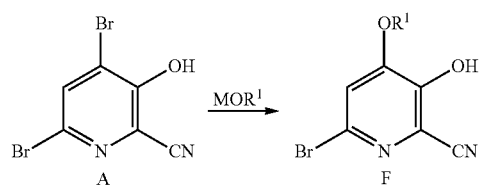

ethoxide), 1-propanol (for 1-propoxide) or 2-propanol (for 2-propoxide), or mixtures of methanol, ethanol, 1-propanol or 2-propanol with a polar, aprotic co-solvent such as DMSO, DMF, sulfolane or NMP. The reaction may also be conducted with an alkali metal alkoxide in one or more of the polar, aprotic solvents in the absence of an alcohol co-solvent. The temperature at which the reaction is conducted is between about 20° C. and about 150° C., preferably between about 40° C. and about 100° C. The substitution reaction generally requires from about 1 to about 48 hours to proceed to completion and may be conducted under pressure in a sealed vessel to prevent the loss of volatile solvents. After the reaction is complete, the desired product is recovered by employing standard isolation and purification techniques.

In some embodiments the preparation of the compound of Formula F from the compound of Formula A may be conducted by employing solvent mixtures including at least one of a protic solvent and a polar aprotic solvent whereby the volume percent (vol %) ratio of the protic solvent to the polar aprotic solvent in the total solvent mixture ranges from about 100:0 to about 0:100. In some embodiments the volume percent (vol %) ratio of the protic solvent to the polar aprotic solvent in the total solvent mixture is 80-100 vol % protic solvent to 0-20 vol % polar aprotic solvent, 60-80 vol % protic solvent to 20-40 vol % polar aprotic solvent, 40-60 vol % protic solvent to 40-60 vol % polar aprotic solvent, 20-40 vol % protic solvent to 60-80 vol % polar aprotic solvent, or 0-20 vol % protic solvent to 80-100 vol % polar aprotic solvent. Preferable volume percent (vol %) ratios of the protic solvent to the polar aprotic solvent are Scheme II

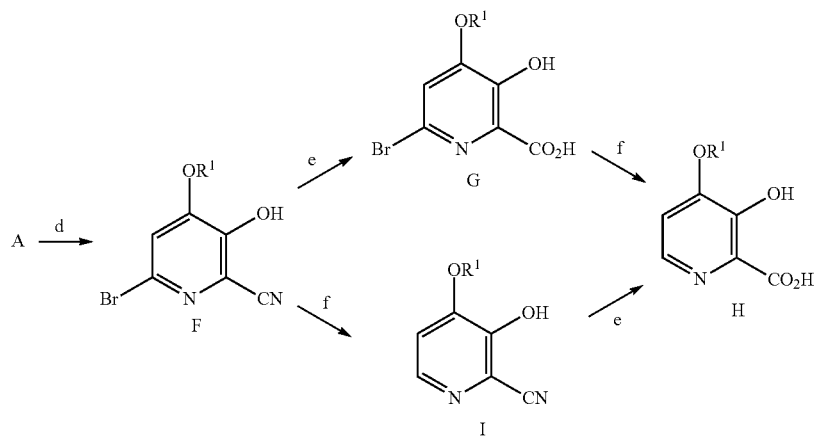

from about 0.01-10 vol % protic solvent to about 90-99.99 vol % polar aprotic solvent. In some embodiments the solvent mixtures used to prepare the compound of Formula F ($R^1$=$CH_3$) from the compound of Formula A are methanol and DMSO, methanol and DMF, methanol and sulfolane, or methanol and NMP.

In the hydrolysis reaction of the nitrile group of the 4-alkoxy-3-hydroxypicolinonitriles of Formulas F and I to produce the 4-alkoxy-3-hydroxypicolinic acids of Formulas G and H, respectively (Steps e in Scheme II), the starting picolinonitriles are typically suspended in a strong, aqueous mineral acid reaction medium and heated for a period of time at elevated temperature with good mixing. Strong mineral acids useful in the hydrolysis reaction include sulfuric acid, phosphoric acid, hydrochloric acid and hydrobromic acid. Preferred, strong mineral acid reaction mediums include aqueous sulfuric acid mixtures such as about 25%, about 30%, about 35%, about 40%, about 45%, about 50%, about 55%, about 60%, about 65%, about 70%, about 75% or about 80% sulfuric acid in water on a weight basis. Most preferably, from about 25% to about 70% sulfuric acid in water may be used. The temperature at which the hydrolysis reaction may be conducted is usually between about 75° C. and about 150° C. and preferably between about 80° C. and about 120° C. The hydrolysis reaction generally requires from about 8 to about 48 hours, preferably from about 8 to about 36 hours, to reach completion. After the reaction is complete, the desired product bromopyridine substrate. Exemplary solvents for use in this reaction include methanol, ethanol, isopropanol, ethyl acetate, and acetic acid. A soluble base such as, for example, triethylamine is normally used in the catalytic reduction with hydrogen.

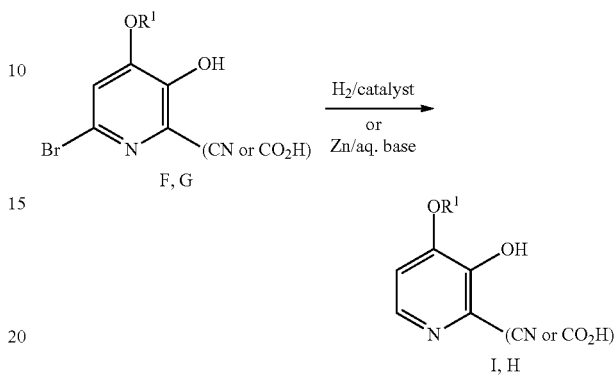

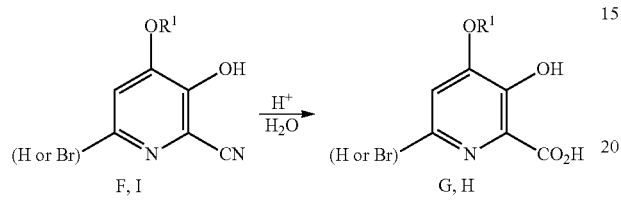

is recovered by cooling and slowly pouring the reaction mixture into cold water and employing standard isolation and purification techniques.

In some embodiments, the hydrolysis reaction of the nitrile group of the 4-alkoxy-3-hydroxypicolinonitriles of Formulas F and I to produce the 4-alkoxy-3-hydroxypicolinic acids of Formulas G and H, respectively (Steps e in Scheme II), the starting picolinonitriles are suspended in an aqueous reaction medium containing a strong base, such as an hydroxide of an alkali or alkaline earth metal, and heated for a period of time at elevated temperature with good mixing. Strong bases for use in the hydrolysis of the picolinonitriles include sodium hydroxide and potassium hydroxide. The concentration of the strong base used in the hydrolysis of the picolinonitriles may range from about 10 to about 40 weight percent (wt %), from about 15 to about 40 wt %, from about 20 to about 40 wt %, from about 30 to about 40 wt %, or from about 15 to about 25 wt %. The molar equivalent ratio of strong base to the nitrile starting material for the hydrolysis reaction may range from about 3:1 to about 10:1, preferably from about 4:1 to about 7:1. The temperature at which the strong base hydrolysis reaction may be conducted is usually between about 75° C. and about 150° C. and preferably between about 80° C. and about 120° C. The strong base hydrolysis reaction generally requires from about 8 to about 48 hours, preferably from about 8 to about 36 hours, to reach completion. After the hydrolysis reaction is complete, the desired product may be isolated by acidifying the reaction mixture and employing standard isolation and purification techniques.

Removal of the bromo group from the 6-position of the compound of Formula F or the compound of Formula G, to produce the reduced products of Formulas I and H, respectively (Steps f in Scheme II), may be achieved by: (1) catalytic reduction using a hydrogen source and a transition metal catalyst, or (2) reduction with a metal such as zinc and a base such as potassium hydroxide or sodium hydroxide.

In the catalytic reduction with hydrogen, suitable hydrogen sources include hydrogen gas or hydrogen transfer reagents such as ammonium, potassium or sodium formate. Suitable transition metal catalysts include, but are not limited to, palladium on carbon (Pd/C) and Raney nickel (Ra/Ni). These catalysts may be used at levels from about 0.01% to about 10% on a weight basis of the metal to the From about 2 to about 4 molar equivalents of the soluble base are normally used. When hydrogen gas is used as the hydrogen source, the reduction reaction may be conducted under an atmospheric pressure of hydrogen gas, or at elevated pressures of hydrogen gas such as 10, 20, 30, 40, 50, 60, 70, 80, 90, 100 pounds or more, per square inch (psi) above atmospheric pressure, or incremental hydrogen gas pressures between these values. It is preferable to use the catalytic reduction chemistry for the reduction of the 6-bromopicolinic acid of Formula G to produce the picolinic acid of Formula H. After the catalytic reduction reaction is complete, the desired product is recovered by employing standard isolation and purification techniques.

In the reduction of compounds of Formulas F and G using a metal such as zinc, the bromopyridine substrate (F, G) is dissolved in an aqueous basic solvent medium and then treated with zinc metal. From about 1 to about 4 molar equivalents of zinc metal (i.e., Zn dust, Zn powder, or a high surface area Zn solid), preferably 1-3 molar equivalents, may be used. The reduction is normally conducted in an aqueous solvent medium of water containing a metal hydroxide such as potassium or sodium hydroxide, where the concentration of the metal hydroxide in water may range from about 10 weight % to about 30 weight %. The reaction may be conducted at a temperature from about 10° C. to about 60° C., preferably from about 20° C. to about 55° C., for a period of about 5 to about 36 hours. It is preferred to use the metal reduction chemistry (i.e., Zn/metal hydroxide) for the reduction of the 6-bromopicolinonitrile of Formula F to produce the picolinonitrile of Formula I. After the metal reduction reaction is complete, the desired product is recovered by using a mineral or organic acid workup and then employing standard isolation and purification techniques.

In one embodiment, the reductive removal of the bromo group and hydrolysis of the nitrile group of the compound of Formula F to produce the compound of Formula H can be conducted in a one-pot process using zinc metal (i.e., Zn dust, Zn powder, or a high surface area Zn solid) and potassium hydroxide at elevated temperature. The temperature at which the one-pot process may be conducted is usually between about 75° C. and about 125° C. and preferably between about 80° C. and about 100° C. After the reaction is complete, the desired product may be isolated by acidifying the reaction mixture and employing standard isolation and purification techniques.

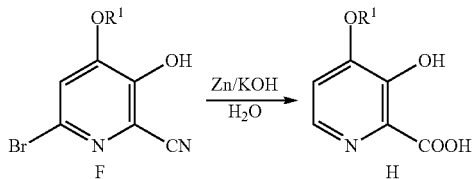

The products obtained by any of these processes, can be recovered by conventional means, such as evaporation, filtration or extraction, and can be purified by standard procedures, such as by recrystallization or chromatography.

The following examples are presented to illustrate the disclosure.

EXAMPLES

Example 1a

Cyano(furan-2-yl)methanaminium bromide

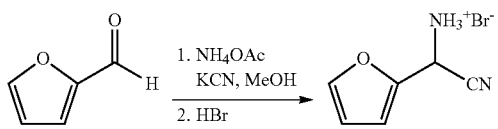

To a magnetically stirred suspension of potassium cyanide (29.3 g, 450 mmol) and ammonium acetate (116 g, 1500 mmol) in methanol (200 mL) was added furan-2-carbaldehyde (28.8 g, 300 mmol) at 0-5° C. The reaction mixture was stirred at 0-5° C. for 40-50 hours. After the reaction was complete as indicated by HPLC analysis, the reaction mixture was diluted with $CH_2Cl_2$ (300 mL) and 5% $NaHCO_3$ (300 mL). The aqueous layer was extracted with additional $CH_2Cl_2$ (4×150 mL). The organic layers were combined and concentrated under vacuum with EtOAc. The resulting residual solution was dissolved in additional EtOAc (600 mL) and cooled to 5° C. A solution of 33% HBr (66.1 g, 270 mmol) in acetic acid was charged slowly to the EtOAc solution to precipitate a solid. The solid was filtered and washed with EtOAc. The collected solid was dried in air at room temperature to give cyano(furan-2-yl)methanaminium bromide (47 g) in 77% yield: $^1$H NMR (400 MHz, DMSO-$d_6$) δ 9.39 (s, 3H), 7.94 (dd, J=1.9, 0.8 Hz, 1H), 6.80 (dt, J=3.4, 0.7 Hz, 1H), 6.63 (dd, J=3.4, 1.9 Hz, 1H), 6.29 (d, J=1.8 Hz, 1H); $^{13}$C NMR (101 MHz, DMSO-$d_6$) δ 145.60, 142.13, 114.28, 112.43, 111.53, 37.54; HBr salt HRMS-ESI (m/z) calc'd for $[C_6H_6N_2O]^+$, 122.048 found, 123.055 [M+H]$^+$; m.p. decomposed >120° C.

Example 1b

Cyano(furan-2-yl)methanaminium bromide

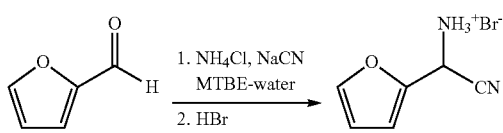

To a magnetically stirred suspension of ammonium chloride (25.03 g, 468 mmol) in MTBE (250 mL) was added furan-2-carbaldehyde (28.8 g, 300 mmol) and a solution of sodium cyanide (17.20 g, 351 mmol) in water (80 mL) at room temperature. The reaction mixture was stirred at room temperature for 15 hours. After the reaction was complete, the aqueous layer was removed. The organic layer was washed with saturated $NaHCO_3$ solution (2×100 mL). The organic layer was dried over $Na_2SO_4$ and filtered. The resulting filtrate was cooled to 5° C. and a solution of 33% HBr (57.4 g, 234 mmol) in acetic acid was charged slowly into the solution to precipitate a solid. The solid was filtered and washed with MTBE. The collected solid was dried in air at room temperature to give cyano(furan-2-yl)methanaminium bromide (29 g) in 54% yield. This sample exhibited similar spectral properties to the sample prepared in Example 1a.

Example 1c 4,6-Dibromo-3-hydroxypicolinonitrile

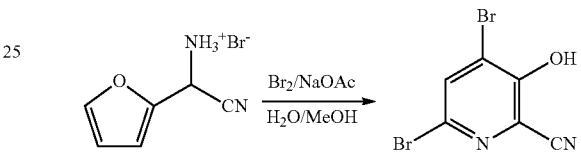

To a mechanically stirred solution of cyano(furan-2-yl) methanaminium bromide (143 g, 704 mmol) in water (1408 mL) at 5° C. was slowly added $Br_2$ (225 g, 1409 mmol) from a dropping funnel while maintaining the temperature at <15° C. After a further 10-15 minutes (after bromine addition was complete), sodium acetate (144 g, 1761 mmol) and methanol (281 mL) were added to the reaction mixture, followed by the dropwise addition of a second portion of $Br_2$ (109 mL, 338 g, 2113 mmol) while maintaining the temperature at <20° C. The reaction mixture was then stirred overnight at room temperature. After the reaction was complete as indicated by HPLC analysis, the reaction mixture was cooled to 5-10° C., and slowly charged with an aqueous solution of 20% $NaHSO_3$ (704 mL) while keeping the temperature at <20° C. The resulting suspension was stirred for 0.5 hr and then filtered. The filter cake was washed with water, dried in air for several hours and then in a vacuum oven at 50° C. overnight to give 4,6-dibromo-3-hydroxypicolinonitrile (137 g) as a light yellow solid in 70% yield: $^1$H NMR (400 MHz, DMSO-$d_6$) δ 8.28 (s, 1H); $^{13}$C NMR (101 MHz, DMSO-$d_6$) δ 155.55, 135.72, 129.81, 125.96, 121.61, 114.58; HRMS-ESI (m/z) calc'd for $[C_6H_2Br_2N_2O]^+$, 275.8534. found, 275.851; mp 183-185° C.

Example 1d 4,6-Dibromo-3-hydroxypicolinonitrile (1-pot process)

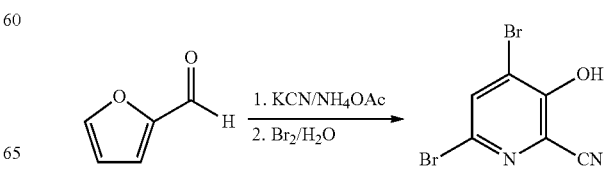

To a magnetically stirred suspension of potassium cyanide (7.16 g, 110 mmol) and ammonium acetate (10.02 g, 130 mmol) in methanol (50 mL) was added furan-2-carbaldehyde (9.61 g, 100 mmol) at room temperature. The reaction mixture was stirred at room temperature overnight. After the reaction was complete as indicated by HPLC analysis, the reaction mixture was diluted with water (100 mL) and cooled to 5° C. Bromine (80 g, 500 mmol) was charged slowly to the reaction while maintaining the temperature at <20° C. The reaction mixture was warmed and stirred overnight at room temperature. After the reaction was complete as indicated by HPLC analysis, the reaction mixture was cooled to 5-10° C., and an aqueous solution of 10% NaHSO$_3$ (100 mL) was slowly charged while maintaining the temperature at <20° C. The resulting suspension was stirred for 0.5 hr and then filtered. The filter cake was washed with water, dried in air for several hours and then in a vacuum oven at 50° C. overnight to give 4,6-dibromo-3-hydroxypicolinonitrile (8 g) as a brown solid in 28% yield. $^1$H NMR (400 MHz, DMSO-d6) δ 11.67 (s, 1H), 8.19 (dd, J=4.4, 1.3 Hz, 1H), 7.56 (dd, J=8.6, 4.4 Hz, 1H), 7.47 (dd, J=8.6, 1.4 Hz, 1H); $^{13}$C NMR (101 MHz, DMSO) δ 157.69, 142.01, 128.86, 124.41, 120.31, 115.99.

Example 1e 4,6-Dibromo-3-hydroxypicolinonitrile (two step process)

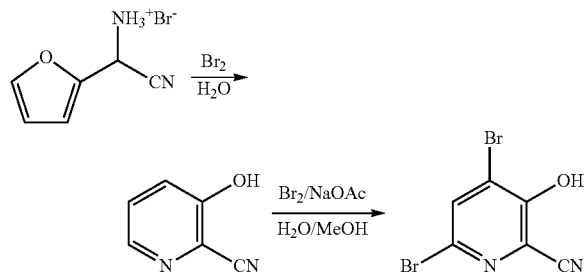

To a mechanically stirred solution of cyano(furan-2-yl) methanaminium bromide (10.15 g, 50 mmol) in water (100 mL) at 5° C. was slowly added Br$_2$ (15.98 g, 100 mmol) from a dropping funnel while maintaining the temperature at <15° C. After a further 30 minutes the reaction mixture was slowly charged with an aqueous solution of 20% NaHSO$_3$ (50 mL) while keeping the temperature at <20° C. The resulting suspension was stirred for 0.5 hr and then filtered. The filter cake was washed with water, dried in air for several hours and then in a vacuum oven at 50° C. overnight to give 3-hydroxypicolinonitrile (2.4 g) as a brown solid in 40% yield: $^1$H NMR (400 MHz, DMSO-d6) δ 11.67 (s, 1H), 8.19 (dd, J=4.4, 1.3 Hz, 1H), 7.56 (dd, J=8.6, 4.4 Hz, 1H), 7.47 (dd, J=8.6, 1.4 Hz, 1H); $^{13}$C NMR (101 MHz, DMSO) δ 157.69, 142.01, 128.86, 124.41, 120.31, 115.99; mp 203° C.

To a mechanically stirred solution of 3-hydroxypicolinonitrile (12.01 g, 100 mmol) and sodium acetate (16.4 g, 200 mmol) in water (150 mL) and methanol (50 mL) at 5° C. was slowly added Br$_2$ (47.9 g, 300 mmol) from a dropping funnel while maintaining the temperature at <20° C. The reaction mixture was then stirred overnight at room temperature. After the reaction was complete as indicated by HPLC analysis, the reaction mixture was cooled to 5-10° C., and slowly charged with an aqueous solution of 20% NaHSO$_3$ (100 mL) while keeping the temperature at <20° C. The resulting suspension was stirred for 0.5 hr and then filtered. The filter cake was washed with water, dried in air for several hours and then in a vacuum oven at 50° C. overnight to give 4,6-dibromo-3-hydroxypicolinonitrile (27 g) as a light yellow solid in 97% yield. The sample exhibited similar spectral properties to other samples of 4,6-dibromo-3-hydroxypicolinonitrile prepared herein.

Example 1f 4,6-Dibromo-3-hydroxypicolinonitrile (biphasic process)

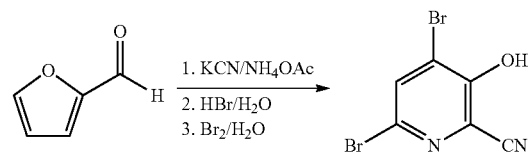 [SMILES: O=Cc1ccco1 ; N#Cc1nc(Br)cc(Br)c1O]

To a magnetically stirred suspension of potassium cyanide (103 g, 1575 mmol) and ammonium acetate (347 g, 4500 mmol) in ethyl acetate (1500 mL) and water (375 mL) was added furan-2-carbaldehyde (144 g, 1500 mmol) at room temperature. The reaction mixture was stirred at room temperature overnight. After the reaction was complete as indicated by $^1$H NMR analysis, the reaction mixture was diluted with 20% Na$_2$CO$_3$ (750 mL). After phase separation, the organic layer was washed with a saturated solution of aqueous NaCl (375 mL). The organic layer containing 2-amino-2-(furan-2-yl)acetonitrile was extracted with 1953 mL of 3.7% aqueous hydrobromic acid (HBr) solution. The organic layer was extracted with additional water (2×200 mL). The combined aqueous layers were cooled to 5° C. and bromine (959 g, 6000 mmol) was charged slowly via use of a peristaltic pump and Teflon tubing to the HBr solution while maintaining the temperature at <20° C. The reaction mixture was then warmed and stirred overnight at 25° C. After the reaction was complete, as indicated by $^1$H NMR analysis, the reaction mixture was cooled to 5-10° C., and then an aqueous solution of 40% NaHSO$_3$ (400 mL) was slowly charged while maintaining the temperature at <20° C. The resulting suspension was stirred for 0.5 hr and then filtered. The filter cake was washed with water (2×200 mL), and dried at ambient temperature in the air to give 4,6-dibromo-3-hydroxypicolinonitrile (251 g) as a tan solid in 60% yield. $^1$H NMR (400 MHz, DMSO-d6) δ 8.28 (s, 1H); $^{13}$C NMR (101 MHz, DMSO-d6) δ 155.57, 135.72, 129.77, 125.97, 121.60, 114.59. HRMS-ESI (m/z) calc'd for [C$_6$H$_2$Br$_2$N$_2$O]$^+$, 275.8534. found, 275.8510. The tan solid was found to contain about 94.5% of 4,6-dibromo-3-hydroxypicolinonitrile and less than about 6% of a monobrominated intermediate product which was tentatively assigned as either 4-bromo-3-hydroxypicolinonitrile or 6-bromo-3-hydroxypicolinonitrile as determined by MS analysis.

Example 1g

4,6-Dibromo-3-hydroxypicolinonitrile (biphasic process)

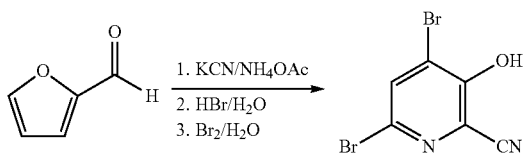 [SMILES: O=Cc1ccco1 ; N#Cc1nc(Br)cc(Br)c1O]

A 30 L jacketed glass reactor was charged with ammonium acetate (3371 g, 43.73 mol), ethyl acetate (13,144 g), potassium cyanide (1,000 g, 15.38 mol), and then water (1819 g). The agitation was turned on to 150 rpm, and then furfural (1,398 g, 14.56 mol) was fed into the reactor via a pump at room temperature. The reaction was allowed to stir overnight at room temperature, at which point the reaction was >97% complete as determined by $^1$H NMR analysis. A solution of 16% sodium carbonate in water (7300 g) was added to the reaction mixture. The reaction mixture was allowed to stir for 1 h. After settling, the aqueous phase was removed, and then the organic phase was washed with saturated brine (5677 g, 23%). After removing the brine, the organic solution was transferred via pump to a 50 L jacketed glass reactor which contained DI water (8896 g). 48% aqueous HBr (2466 g, 14.6 mol) was diluted with DI water (5668 grams) and the resulting HBr solution was then pumped into the 50 L reactor with the agitation at 150 rpm at room temperature. After allowing the mixture to stir for 1 hour, the phases were allowed to separate for 45 minutes. The aqueous phase was drained into two 5 gallon carboys. The organic phase was then washed 2 times with about 2,000 gram of DI water. The DI water washes were placed in the carboys. The organic phase was discarded and then the 50 L reactor was washed with 500 mL of ethyl acetate and 500 mL of DI water. The aqueous phase (24,536 grams) in the two carboys was transferred back to the 50 L reactor, and then the residual HBr salt in the carboys was washed into reactor with a total of 1945 grams of DI water. The aqueous phase in the reactor was then cooled to about 0° C. and allowed to mix overnight. Bromine (9311 grams, 56.1 mol) was then added to the reaction over 45 minutes (initial temperature of about 0° C.), which resulted in a temperature rise to 25° C. During the bromine addition, a material precipitated from solution and then re-dissolved. About 1 h after the feed of bromine was completed, solids began to reform in the solution. The reaction was then heated at 35° C. for about 24 h. The reaction was then cooled to <10° C., and then 40% aqueous sodium bisulfite (3757 g) was added to quench the excess bromine. The solids were collected by filtration and washed with DI water (5 L) until the wash liquid was colorless. The resulting wet cake was allowed to dry in glass trays until no further weight loss was observed, which resulted in 2590 grams of a free flowing tan powder. $^1$H NMR assay indicated that the solid was 97.8 wt % 4,6-dibromo-3-hydroxy-picolinonitrile. The yield based on the assay was 62.6%. $^1$H NMR (400 MHz, DMSO-d6) δ 8.28 (s, 1H), 7.75 (d, J=8 Hz, 0.03H), 7.43 (d, J=8 Hz, 0.03H); $^{13}$C NMR (101 MHz, DMSO) δ 155.47, 135.68, 129.86, 125.88, 125.88, 121.63, 114.50. HRMS (m/z) Positive Ion mode [M+1] calcd for $[C_6H_3Br_2N_2O]^+$ 276.8607. found 276.8609.

Example 1h

3-Hydroxypicolinonitrile (biphasic process)

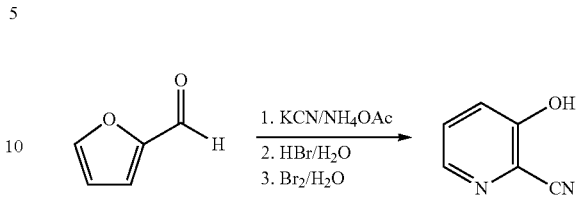

To an inerted 6 L straight-walled jacketed reactor was added 346 grams of ammonium acetate (4500 mmol), 1500 mL of ethyl acetate (EtOAc), 300 mL of DI water, and 102.5 grams of potassium cyanide (KCN, 1574 mmol). The KCN jar and addition funnel were then rinsed with about 75 mL of water to wash any residual KCN into the reactor. The reaction vessel was closed, cooled to 15° C. and the agitation was then set to 260 rpm. Furfural (144 g, 1500 mmol) was then added to the reactor via syringe over 5 minutes. The temperature in the reactor increased from about 15° C. to 22° C. The reaction was allowed to stir overnight (22° C.). The agitation was turned off to allow the phases to be separated. The organic phase was then sampled for $^1$H NMR analysis. The reaction was shown to be >99% converted to the desired product. With agitation (250 rpm), 750 mL of 20% aqueous sodium carbonate was added to the reactor and allowed to stir for 10 minutes. The aqueous phase containing the sodium carbonate solution was removed and then the remaining organic phase was washed with 400 mL of saturated brine. 170 mL of aqueous 48% HBr (1 equiv., 1345 mmol) diluted in about 1300 ml of DI water was added to the reactor containing the organic phase. The reactor containing the aqueous HBr-organic phase was mixed (250 rpm) for 15 minutes. After settling, the aqueous layer was drained into a 5 L receiving vessel. The organic layer was then washed with an additional 250 mL of DI water which was also drained into the 5 L vessel. The reactor was then emptied and rinsed with 300 mL of EtOAc. The aqueous layer in the 5 L vessel was then vacuum transferred back up to the 5 L straight-walled reactor. The 5 L receiving vessel was washed with 200 mL of water which was also added to the reactor. The contents of the reactor were then agitated, cooled to 0° C. and then bromine (240 g, 1500 mmol) was added via a Teflon line through a peristaltic pump over 30 minutes, which led to a temperature rise to 19° C. and the formation of a precipitate. The reaction was allowed to stir overnight at room temperature. 40% aqueous sodium bisulfite (250 mL) was then added slowly to the reaction to maintain a temp <40° C. After the bromine was quenched, the solids were collected on a frit and washed with water and dried to yield 3-hydroxypicolinonitrile in 47% yield (85 g) as a red crystalline solid. $^1$H NMR (400 MHz, DMSO-d$_6$) δ 11.67 (s, 1H), 8.21 (dd, J=4.4, 1.4 Hz, 1H), 7.57 (dd, J=8.6, 4.4 Hz, 1H), 7.50 (dd, J=8.6, 1.4 Hz, 1H)$^{13}$C NMR (101 MHz, DMSO) δ 157.66, 141.92, 128.72, 124.35, 120.34, 115.97. HRMS (m/z) Positive Ion mode [M+1] calcd for $[C_6H_5N_2O]^+$ 121.0397. found 121.0400.

Example 2a

6-Bromo-4-methoxy-3-hydroxypicolinonitrile

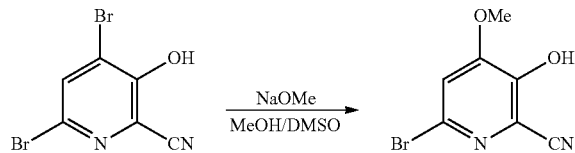 [SMILES: N#Cc1nc(Br)cc(Br)c1O ; COc1cc(Br)nc(C#N)c1O ; "NaOMe"]

To a magnetically stirred solution of 4,6-dibromo-3-hydroxypicolinonitrile (152 g, 547 mmol) in DMSO (820 mL) was added a 30% NaOMe in MeOH (492 g, 2.73 mol) solution at room temperature. The reaction mixture was warmed to 50-55° C. and stirred overnight. The reaction mixture was then cooled to 15-20° C., quenched by slow addition of 1.5N HCl (1500 mL) to adjust the pH to about 2-3, and then extracted with $CH_2Cl_2$ (2×1000 mL). The combined organic layers were washed with 0.1N HCl (1000 mL) and concentrated to ca. 500 ml volume, charged with 100 mL of acetonitrile (ACN), and finally concentrated to dryness. The crude product obtained was washed with 0.1N HCl (1000 mL) and filtered. The filter cake was washed with water, dried in air for several hours and then in a vacuum oven at 50° C. overnight to give 6-bromo-3-hydroxy-4-methoxypicolinonitrile (83 g) in 66% yield as a brown solid: $^1H$ NMR (400 MHz, DMSO-d6) δ 11.64 (s, 1H), 7.48 (s, 1H), 3.97 (s, 3H); $^{13}C$ NMR (101 MHz, DMSO-d6) δ 156.54, 149.35, 131.02, 118.54, 114.91, 114.57, 57.20; HRMS-ESI (m/z) calc'd for $[C_7H_5BrN_2O_2]^+$, 227.9533. found, 227.9534; m.p. 168° C. The aqueous filtrate was extracted with $CH_2Cl_2$ (twice). The organic layers were combined and concentrated with ACN as described herein. The crude solid was dissolved in ACN (50 mL) and added slowly into 0.1N HCl (400 mL) at room temperature. The precipitated solid was stirred for 1 h and filtered. The filter cake was washed with water and dried to give additional 6-bromo-3-hydroxy-4-methoxypicolinonitrile (13 g) in 10% yield.

Example 2b

6-Bromo-4-methoxy-3-hydroxypicolinonitrile

4,6-dibromo-hydroxypicolinonitrile (500 grams, 1806 mmol) was dissolved in a mixture of 500 mL of anhydrous DMSO and 20 mL of anhydrous MeOH at room temperature under an inert atmosphere. Sodium methoxide (250 grams, 4606 mmol) and 500 mL of anhydrous DMSO were then charged to a 5-L, 4-neck reaction flask which had been purged with nitrogen. The reaction flask was outfitted with a condenser (w/$N_2$ line), thermal well, mechanical stirrer and a septum (with a ⅛" feed line). The solution of the 4,6-dibromo-hydroxypicolinonitrile in DMSO-MeOH was then fed to the reaction flask at a rate of 15-20 g per minute via a peristaltic pump through the ⅛" Teflon tubing. When the reaction temperature reached 55° C., a cold water bath was placed around the flask. The reaction was maintained between 50 and 55° C. during the feed. The reaction was then maintained at around 54° C. for 1.5 h after addition was complete. After determining the reaction was complete by $^1H$ NMR analysis, the reaction mixture was cooled to <30° C. with an ice bath. At 30° C., 2 L of water were added to the reaction mixture which caused the solution to warm to >40° C. The reaction mixture was cooled to 30° C., and then 10 N sulfuric acid was added via an addition funnel until the pH was around 2.5, which resulted in the precipitation of a white solid. At pH 2.5, the reaction was allowed to stir for 30-60 minutes during which time the reaction mixture was cooled to 15° C. The solid was filtered and then washed with water until the filtrate was colorless. The solid was dried in a vacuum oven at 50° C. until the weight remained constant. The solid was a slightly tan colored powder (344 g, 83% yield): $^1H$ NMR (400 MHz, DMSO-d6) δ 11.64 (s, 1H), 7.48 (s, 1H), 3.97 (s, 3H); $^{13}C$ NMR (101 MHz, DMSO-d6) δ 156.54, 149.35, 131.02, 118.54, 114.91, 114.57, 57.20.

Example 2c

6-Bromo-4-methoxy-3-hydroxypicolinonitrile

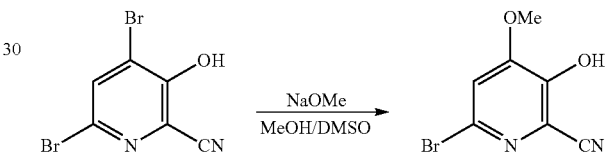

25.1 kg of dimethyl sulfoxide (DMSO) was loaded into a glass lined steel (GLS) reactor and heated under jacket temperature control set point of 100° C. with a purge of nitrogen at 4 liter/min at atmospheric pressure for 18 hours. The jacket temperature was reduced to 35° C. and the DMSO was allowed to cool. 4,6-dibromo-3-hydroxypicolinonitrile (8.0 kg, 28.8 mol) was loaded in to the reactor with the vent open and a 1 liter/min nitrogen purge. The reactor was set to control pressure at 25 mm Hg (actual pressure controlled at a nominal pressure of 35-60 mm Hg), agitated at 90 rpm and put under master temperature control, which utilized the actual reaction mixture, of 30° C. The overhead heat exchanger, used to condense methanol, was operated at −5 to −10° C. A 25% by weight sodium methoxide mixture in methanol (16.51 Kg, 76.4 mol) was pumped into the reactor over about 30-45 minutes. Methanol was continuously stripped from the reaction mixture and condensed. After the methoxide had been added, the reaction temperature was increased to 53° C. over 1.5 hours. Approximately 5.5 hours after reaching 52-53° C., the reaction was sampled and determined to be complete by $^1H$ NMR. The reaction mixture was cooled under a jacket control temperature of 35° C. and methanol was flushed through process sample lines and the sodium methoxide feed addition pump. 25 kg of de-ionized (DI) water was added to the reaction mixture and the entire contents transferred to a stainless steel (SS) reactor. An additional 25 kg of DI water was loaded into the GLS reactor and the contents transferred to the SS reactor. 26.6 kg of a 20% aqueous sulfuric acid mixture was added to the basic (pH 13) aqueous reaction product, sodium 6-bromo-2-cyano-4-methoxypyridin-3-olate, to result in a pH<2. The neutralized 6-bromo-4-methoxy-3-hydroxy picolinonitrile was isolated using a centrifuge. The wetcake was washed using 5 gallons of DI water that was loaded into the SS reactor to flush residual solids to the centrifuge. The solids were spun dry under nitrogen in the centrifuge and the wetcake was further dried under a purge of dry nitrogen until no further weight loss was observed. 5.011 kg of dried 6-bromo-4-methoxy-3-hydroxypicolinonitrile was obtained as an off-white solid (76% yield). $^1$H NMR assay of the material indicated that the product was >99.5% pure.

Example 2d

6-Bromo-4-methoxy-3-hydroxypicolinonitrile

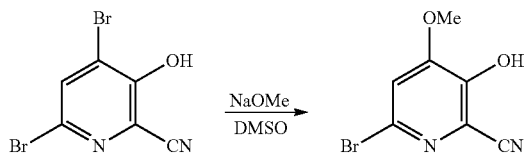 [SMILES: N#Cc1nc(Br)cc(Br)c1O ; COc1cc(Br)nc(C#N)c1O ; "NaOMe"]

To a slurry of sodium methoxide (15.2 g, 282 mmol) in 35 mL of anhydrous dimethyl sulfoxide (DMSO) was added a solution of 4,6-dibromo-3-hydroxypicolinonitrile (30 g, 108 mmol) in anhydrous DMSO (30 mL). The solution was added over 30 minutes and the reaction mixture was maintained below 55° C. during the addition. The reaction solution was heated for an additional 1.5 hours after the feed was complete. The resulting reaction mixture was cooled to <30° C., and then 120 mL of DI water was added. The reaction mixture was allowed to cool to about 25° C. The pH of the reaction mixture was adjusted to about 2 with 40% sulfuric acid, which resulted in the precipitation of a solid. The solid were collected by filtration, washed with 75 mL of pH 1.5 sulfuric acid followed by 25 mL of DI water. The solid was then allowed to dry to yield 20.7 g (83.7% yield) of desired product. $^1$H NMR (400 MHz, DMSO-$d_6$) δ 11.60 (s, 1H), 7.47 (s, 1H), 3.98 (s, 3H). $^{13}$C NMR (101 MHz, DMSO) δ 156.52, 149.35, 130.99, 118.55, 114.89, 114.52, 57.18.

Example 2e

6-Bromo-4-methoxy-3-hydroxypicolinonitrile

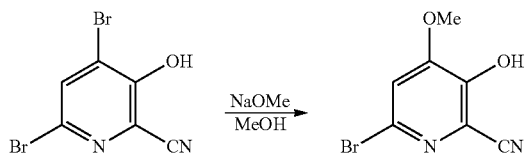 [SMILES: "MeOH" ; N#Cc1nc(Br)cc(Br)c1O ; COc1cc(Br)nc(C#N)c1O ; "NaOMe"]

To a solution of 4,6-dibromo-3-hydroxypicolinonitrile (1.11 g, 4.0 mmol) in methanol (7.5 mL) in a 40 mL microwave tube was added a solution of 25 wt % NaOMe in MeOH (2.59 g, 12 mmol). The solution was heated at 110° C. under microwave irradiation for 12 h. The reaction mixture was then cooled to 15-20° C., quenched by slow addition of 2 M HCl to adjust the pH to about 4-5. The reaction mixture was concentrated by rotary evaporation. The mixture was purified by flash chromatography on silica gel, eluting with methanol/$CH_2Cl_2$ to give 0.53 g (58% yield) of solid (mp=177-180° C.). $^1$H NMR (400 MHz, Methanol-$d_4$) δ 7.33 (d, J=1.0 Hz, 1H), 4.01 (s, 3H). $^{13}$C NMR (101 MHz, Methanol-$d_4$) δ 157.96, 150.91, 132.58, 119.91, 115.50, 115.09, 57.66.

Example 2f

6-Bromo-4-ethoxy-3-hydroxypicolinonitrile

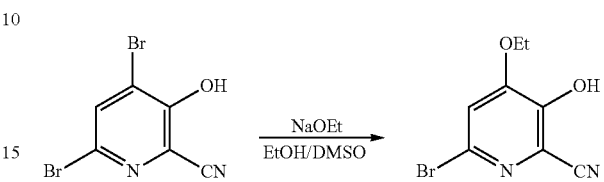

To a magnetically stirred solution of 4,6-dibromo-3-hydroxypicolinonitrile (5.40 g, 19.4 mmol) in DMSO (30 mL) was added a 21% NaOEt in EtOH (31.5 g, 97 mol) solution at room temperature. The reaction mixture was heated at 55° C. for 18 h. The reaction mixture was then cooled to 15-20° C. and poured into a mixture of 25 mL of concentrated HCl and 80 g of ice. A tan precipitate formed. The mixture was extracted into EtOAc (4×75 mL). The combined organics were washed with water (5×100 mL) and then brine. The extracts were dried (MgSO$_4$) and rotary evaporated to a tan solid. The solid was triturated with 1:1 hexane-ether (3×20 mL) and then dried in air to yield a light tan solid (4.39 g, 93% yield, m.p.=175-177° C.). $^1$H NMR (400 MHz, DMSO-$d_6$) δ 11.42 (s, 1H), 7.45 (s, 1H), 4.25 (q, J=7.0 Hz, 2H), 1.38 (t, J=7.0 Hz, 3H). $^{13}$C NMR (101 MHz, DMSO) δ 155.81, 149.32, 131.15, 118.63, 114.94, 114.87, 65.74, 13.94. HRMS-ESI (m/z) calc'd for $[C_8H_7BrN_2O_2]^+$, 241.9691. found, 241.9690.

Example 2g

6-Bromo-3-hydroxy-4-methoxypicolinic acid

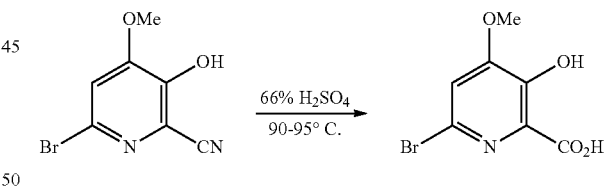

To a magnetically stirred solid sample of 6-bromo-3-hydroxy-4-methoxypicolinonitrile (88 g, 384 mmol) was added 66% $H_2SO_4$ (384 mL) at room temperature. The resulting mixture was warmed and stirred overnight at 90-95° C. After HPLC indicated the reaction was complete, the reaction mixture was cooled to 30-40° C. and transferred slowly to a flask charged with water (3072 g) to precipitate the product. The resulting suspension was stirred for 0.5 hr. The resulting precipitate was filtered, washed with water, and dried in air overnight to give 6-bromo-3-hydroxy-4-methoxypicolinic acid (95 g) as an off-white solid in 100% yield: $^1$H NMR (400 MHz, DMSO-d6) δ 7.48 (s, 1H), 3.97 (s, 3H); $^{13}$C NMR (101 MHz, DMSO-d6) δ 170.12, 156.58, 149.09, 130.19, 129.86, 114.46, 56.79; HRMS-ESI (m/z) [M+H]+ calcd for $C_7H_6BrNO_4$, 246.948. found, 246.948; m.p. 167-170° C.

Example 2h

6-Bromo-4-ethoxy-3-hydroxypicolinic acid

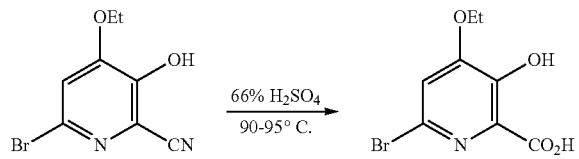 [SMILES: CCOc1cc(Br)nc(C#N)c1O ; "66% H2SO4" ; CCOc1cc(Br)nc(C(=O)O)c1O]

6-Bromo-4-ethoxy-3-hydroxypicolinonitrile (906 mg, 3.73 mmol) was added to 66% $H_2SO_4$ (15 mL) at room temperature. The resulting mixture was magnetically stirred and heated at 90° C. for 17 h, cooled to ambient temperature, and poured into 12 g ice. A solution of 50% NaOH was added until a tan solid precipitated. The solid was extracted into EtOAc (3×25 mL), dried over $MgSO_4$, and rotary evaporated to 923 mg of white crystalline solid (94% yield, m.p.=152-155° C.). $^1H$ NMR (400 MHz, DMSO-$d_6$) δ 11.5 (br, 1H), 7.36 (s, 1H), 4.19 (q, J=7.0 Hz, 2H), 1.36 (t, J=7.0 Hz, 3H). HRMS-ESI (m/z) [M+H]+ calcd for $C_8H_8BrNO_4$, 260.9637. found, 260.964.

Example 2i

3-Hydroxy-4-methoxypicolinic acid

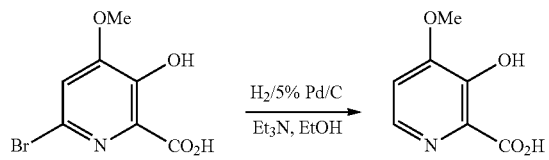

Batch 1: To 3-hydroxy-6-bromo-4-methoxypicolinic acid (47.5 g) and EtOH (576 mL) in a Parr shaker bottle (2 L) was added triethylamine (40.7 g, 402 mmol). Then under a nitrogen atmosphere 5% Pd/C (20 g, 9.6 mmol; 5 mol %) was added to the bottle. The reaction slurry was placed on a Parr shaker and the bottle placed under hydrogen gas (40-45 psi) and shaked. After completion of the reaction as indicated by HPLC analysis, the hydrogen gas was removed under vacuum and replaced with nitrogen gas. The reaction slurry was filtered through a pad of celite and the celite pad was washed with fresh ethanol.

Batch 2: To 3-hydroxy-6-bromo-4-methoxypicolinic acid (47.5 g) and EtOH (576 mL) in a Parr shaker bottle (2 L) was added triethylamine (40.7 g, 402 mmol). Then under a nitrogen atmosphere added 5% Pd/C (10 g, 4.8 mmol; 2.5 mol %). The $2^{nd}$ reaction was completed as described for the $1^{st}$ batch. The ethanolic filtrates for the 2 batches were combined and concentrated to give a solid. The solid was diluted with 0.2N HCl (400 mL) to adjust the pH to about 1-2 and the resulting suspension was stirred for 10-15 minutes at room temperature. The solid was then collected by filtration, washed with water and dried in air for several hours and then in a vacuum oven at 50° C. to give 3-hydroxy-4-methoxypicolinic acid (55 g) as an off-white solid in 85% yield: $^1H$ NMR (400 MHz, DMSO-d6) δ 8.04 (d, J=6.4 Hz, 1H), 7.40 (d, J=6.5 Hz, 1H), 4.04 (s, 3H); $^{13}C$ NMR (101 MHz, DMSO-d6) δ 164.16, 162.03, 152.52, 132.32, 126.57, 109.13, 57.35; HRMS-ESI (m/z) calcd for $C_7H_7NO_4$, 169.0379. found, 169.0375; m.p. 219° C.

Example 2j

3-Hydroxy-4-ethoxypicolinic acid

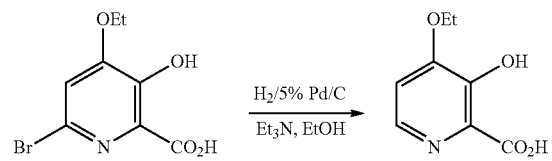 [SMILES: CCOc1cc(Br)nc(C(=O)O)c1O ; CCOc1ccnc(C(=O)O)c1O]

To 6-bromo-4-ethoxy-3-hydroxypicolinic acid (739 mg) and EtOH (20 mL) in a Parr shaker bottle (0.5 L) was added triethylamine (599 mg, 5.92 mmol). 5% Pd/C (300 mg, 0.141 mmol; 5 mol %) was added to the bottle. The reaction mixture was shaken under hydrogen gas (45 psi) for 22 h. The reaction mixture was filtered through a pad of celite, and the celite pad was washed with ethanol. The filtrate was rotary evaporated to a white solid (1.047 g) which was then slurried in 15 mL of 0.1M HCl and filtered. Solid was washed with 5 mL of 0.1M HCl and then 5 mL water. Solid was dried in air to give 402 mg (78% yield, m.p.=216-219° C.) of off-white powder. $^1H$ NMR showed the presence of 7% $Et_3NHCl$ in addition to product resonances. $^1H$ NMR (400 MHz, DMSO-$d_6$) δ 14.4 (br, 1H), 8.01 (d, J=6.4 Hz, 1H), 7.38 (d, J=6.4 Hz, 1H), 4.32 (q, J=7.0 Hz, 2H), 1.41 (t, J=7.0 Hz, 3H). $^{13}C\{^1H\}$ NMR (DMSO-$d_6$. 126 MHz) δ 164.33, 161.13, 152.37, 132.44, 126.92, 109.53, 66.02, 14.05. HRMS-ESI (m/z) [M+H]+ calcd for $C_8H_9BrO_4$, 183.0532. found, 183.0536.

Example 2k

3-Hydroxy-4-methoxypicolinonitrile

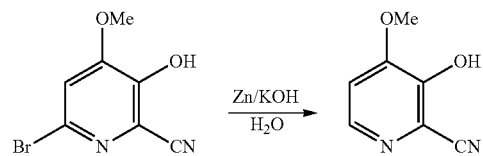 [SMILES: COc1cc(Br)nc(C#N)c1O ; O ; COc1ccnc(C#N)c1O]

A suspension of 6-bromo-3-hydroxy-4-methoxypicolinonitrile (7.5 g, 32.7 mmol), Zn dust (4.28 g, 65.5 mmol) and 20% aqueous KOH (100 mL) was stirred overnight at room temperature. After completion of the reaction as indicated by HPLC analysis, the reaction mixture was filtered through celite. The aqueous filtrate was cooled to 5° C. and adjusted to a pH of about 3-4 with 3N HCl(~125 mL). The precipitated solid was filtered, washed with water and dried in air and then in a vacuum oven at 50° C. to give 3-hydroxy-4-methoxypicolinonitrile (4 g) as a brown solid in 81% yield: $^1H$ NMR (400 MHz, DMSO-d6) δ 11.12 (s, 1H), 8.08 (d, J=5.3 Hz, 1H), 7.28 (d, J=5.3 Hz, 1H), 3.94 (s, 3H); $^{13}C$ NMR (101 MHz, DMSO-d6) δ 154.69, 148.59, 143.51, 119.84, 116.07, 110.54, 56.36; HRMS-ESI (m/z) calcd for $C_7H_6N_2O_2$, 150.043. found, 150.0429; m.p. 224° C.

Example 2l

3-Hydroxy-4-methoxypicolinic acid

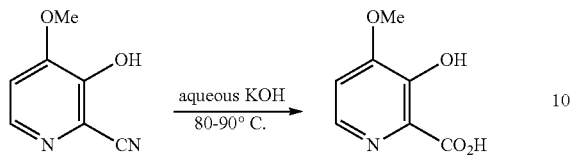

A 1 L, 3-neck round bottom flask was charged with 125 grams of KOH (1952 mmol, 88% assay for KOH) and then 400 grams of water. The flask was outfitted with a mechanical stirrer, thermal well, and a condenser (w/N2 inlet). The solution was mixed until the KOH dissolved. 3-Hydroxy-4-methoxypicolinonitrile (50 g, 334 mmol) was then added to the solution, which did not result in an exotherm. The reaction was heated to 90° C. After the reaction was considered complete by NMR analysis (12 h), the reaction solution was allowed to cool to ambient temperature and allowed to stand overnight. 12N HCl was added until the pH was 2-3, which caused the product to precipitate out of solution. The solids were collected by filtration and washed with 10 mL of MeOH and then 10 mL of MTBE. The product was allowed to dry overnight and then was placed in the vacuum oven for 4 hours at 60° C. 49.2 grams of 3-hydroxy-4-methoxy picolinic acid was obtained as an off-white solid (87.2% yield); $^1$H NMR (400 MHz, DMSO-$d_6$) δ 8.04 (d, J=6.4 Hz, 1H), 7.39 (d, J=6.5 Hz, 1H), 4.04 (s, 3H); $^{13}$C NMR (101 MHz, DMSO-d6) δ 164.16, 162.03, 152.52, 132.32, 126.57, 109.13, 57.35; HRMS-ESI (m/z) calcd for $C_7H_7NO_4$, 169.0379. found, 169.0375.

Example 2m

3-Hydroxy-4-methoxypicolinic acid

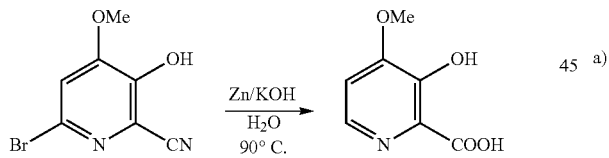

A 1 L, 3-neck round bottom flask with a mechanical stirrer was charged with 6-bromo-3-hydroxy-4-methoxypicolinonitrile (45.8 g, 200 mmol) and zinc dust (14.38 g, 220 mmol) in water (200 mL). 45% KOH (125 g, 1000 mmol) was charged slowly at rt. The reaction was heated to 90° C. After the reaction was considered complete by HPLC analysis (20 h), the reaction solution was allowed to cool to ambient temperature. The reaction mixture was filtered through celite. The filtrate was cooled with an ice bath and then 12N HCl (ca. 90 mL) was added until the pH was 0.9. The solids were collected by filtration and washed with 0.1N HCl and water. The product was allowed to dry overnight and then was placed in the vacuum oven overnight at 50° C. 3-hydroxy-4-methoxy picolinic acid was obtained as an off-white solid (26.9 g, 80% yield): $^1$H NMR (400 MHz, DMSO-d6) δ 8.04 (d, J=6.4 Hz, 1H), 7.39 (d, J=6.5 Hz, 1H), 4.04 (s, 3H); $^{13}$C NMR (101 MHz, DMSO-d6) δ 164.16, 162.03, 152.52, 132.32, 126.57, 109.13, 57.35; HRMS-ESI (m/z) calcd for $C_7H_7NO_4$, 169.0379. found, 169.0375.

Example 2n

3-Hydroxy-4-methoxypicolinic acid

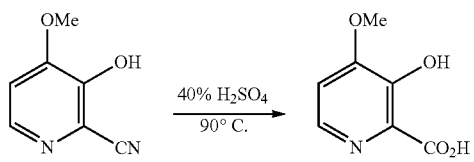 [SMILES: COc1ccnc(C#N)c1O ; "90° C." ; COc1ccnc(C(=O)O)c1O]

To a magnetically stirred solid of 3-hydroxy-6-bromo-4-methoxypicolinic acid (3.9 g, 26 mmol) was added 40% aqueous $H_2SO_4$ (125 mL) at room temperature. The mixture was then warmed and stirred overnight at 90° C. After HPLC analysis indicated the reaction was complete, the reaction mixture was cooled to 5° C., and 25% aqueous NaOH (~250 mL) was charged slowly to the reaction mixture to adjust the pH to about 1-2. The resulting suspension was stirred for 10-15 minutes at room temperature and the solid product was collected by filtration. The filter cake was washed with water and dried in air for several hours and then in a vacuum oven at 50° C. to give 3-hydroxy-4-methoxypicolinic acid (3.1 g) as a brown solid in 70% yield: m.p. 227° C. $^1$H NMR (400 MHz, DMSO-d6) δ 8.04 (d, J=6.4 Hz, 1H), 7.40 (d, J=6.5 Hz, 1H), 4.04 (s, 3H); $^{13}$C NMR (101 MHz, DMSO-d6) δ 164.16, 162.03, 152.52, 132.32, 126.57, 109.13, 57.35.

What is claimed is:

1. A compound selected from the group consisting of:

a) 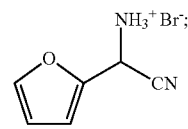

b) 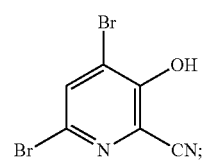

c) 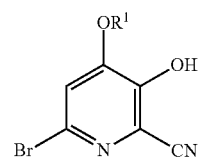

wherein $R^1$ is a $C_1$-$C_3$ alkyl;

d)

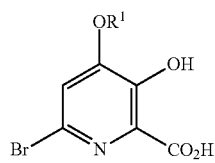

wherein $R^1$ is a $C_1$-$C_3$ alkyl; and e)

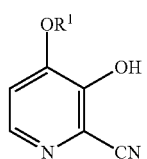

wherein $R^1$ is a $C_2$-$C_3$ alkyl.

2. The compound of claim 1, wherein the compound is:

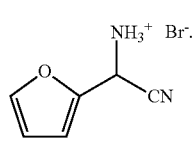

3. The compound of claim 1, wherein the compound is:

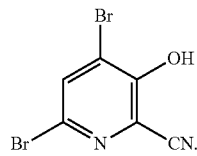

4. The compound of claim 1, wherein the compound is:

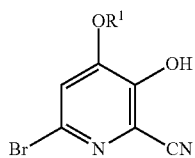

wherein $R^1$ is a $C_1$-$C_3$ alkyl.

5. The compound of claim 4, wherein $R^1$ is methyl.

6. The compound of claim 1, wherein the compound is:

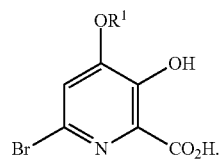

wherein $R^1$ is a $C_1$-$C_3$ alkyl.

7. The compound of claim 6, wherein $R^1$ is methyl.

8. The compound of claim 1, wherein the compound is:

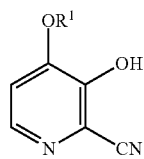

wherein $R^1$ is a $C_2$-$C_3$ alkyl.

9. The compound of claim 8, wherein the compound is:

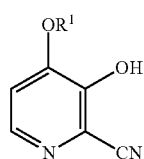

wherein $R^1$ is $C_3$ alkyl.

* * * * *